United States Patent [19]

Wilson

[11] 4,042,367

[45] Aug. 16, 1977

[54] METHOD FOR CONTROLLING THE GROWTH OF AQUATIC PLANTS

[75] Inventor: Charles G. Wilson, Milwaukee, Wis.

[73] Assignee: Aquashade, Inc., Dobbs Ferry, N.Y.

[21] Appl. No.: 217,952

[22] Filed: Jan. 14, 1972

[51] Int. Cl.$^2$ ............................................. A01N 9/14
[52] U.S. Cl. ........................................ 71/66; 260/163; 260/200; 260/456 A; 71/67; 71/103
[58] Field of Search ................................ 71/65, 66, 67

[56] References Cited
PUBLICATIONS

Dolge Co., "New Dolge Lake & Pond Dye" (1970) Data Sheet, pp. 1–2, Sept. 1970.
Dolge – Fairway to Clubhouse, (1970), Golfdom – Jan. 1970.

*Primary Examiner*—Glennon H. Hollrah
*Attorney, Agent, or Firm*—Curtis, Morris & Safford

[57] ABSTRACT

The growth of aquatic plants, and particularly undesirable aquatic plants such as weeds and algae, is controlled by adding a dye to the water in the vicinity of the undesired plant growth. The dye is of a color such that it absorbs a substantial portion of the light at wavelengths normally used by the plants in photosynthesis, so that growth of the plants is stopped or arrested. The color of the dye preferably ranges from blue to green, and preferably is predominantly blue so that the water has a pleasing appearance to the eye. Preferably, the dye is applied prior to germination of the plants and at such further times as necessary.

7 Claims, No Drawings

METHOD FOR CONTROLLING THE GROWTH OF AQUATIC PLANTS

This invention relates to methods and compositions for controlling the growth of aquatic plant life in water, and particularly relates to methods for controlling the growth of weeds, algae and other undesirable plant life.

The eutrophication of inland waters in the United States is a serious problem. Eutrophication may be caused by the discharging into larger bodies of water of wastes having excessive amounts of phosphates and other plant nutrients which greatly accelerate the rate of growth of algae, weeds and other such plants in the water. This is quite undesirable in that it robs other aquatic life such as fish of the oxygen needed for survival, hinders navigation and fishing, and often becalms the circulation of the waters to an extent such that they become putrid.

In smaller lakes and ponds, the excessive growth of weeds can virtually fill the body of water, thus not only ruining it for fishing, boating and swimming, but also making the water ugly and foul-smelling.

In accordance with the foregoing, one of the objects of the present invention is to provide a method for controlling the growth of aquatic plant life. Furthermore, it is an object to provide such a method which is relatively inexpensive to use, is safe to humans and other animal life which may come in contact with the water in which it is used, and which gives the water a pleasing color.

The foregoing objects are met by the provision of a method in which the water in the area of plant growth is colored with a pigment which absorbs light of wavelengths usually used by aquatic plants in the photosynthesis process. Thus, the light at the wavelengths necessary to the growth of the plants is screened from the plants so as to severely stunt or totally inhibit their growth. The coloring process may be repeated as often as necessary during the growing season to hold the growth rate of the plants at an acceptable level. The dyes used preferably color the water a shade ranging from blue to green, but predominantly blue so as to beautify the water as well as free it from excessive plant growth.

Now considering the invention in detail, it is preferred that the water be colored by spreading a dye over the surface of the water in the vicinity of expected plant growth. The first such application preferably is prior to germination of the plant life. The time of germination for aquatic plant life varies with many different factors such as climate, mean temperatures in the vicinity, type of weeds involved, depth of the water, etc. However, the germination time is believed to depend primarily upon the water temperature and the response of the particular plant life to water temperatures to start germination. In portions of the United States and the rest of the world in which ice forms on inland water bodies during the winter, it is preferred that the dye be applied shortly after the ice finally has melted in the spring. Aquatic weed germination usually starts within a few weeks thereafter.

In climes in which ice does not form, such as in Florida and other sub-tropical or tropical areas of the world, the germination period, if any, should be observed empirically. During the growing season, the dye application step should be repeated whenever it is noticed that the plants are growing at an undesirably fast rate. This usually can be determined visually merely by looking at the plants and noticing the growth rate. Alternatively, the dye coloring step can be repeated at fixed time intervals during the growing season, as determined by experience with the particular dyes used, with the particular plants involved, the length of the growing season, the size of the body of water, the degree of circulation of the water, etc.

In general, the frequency of re-application of the dye will vary directly with the length of the growing season for the aquatic plants. It is well known, for example, that the growing season for most plants varies considerably with geographic location. The growing season is shorter in areas closer to the Earth's poles, is shorter in inland areas than in coastal areas of the same latitude, and also decreases with the altitude above sea level. Prevailing winds, droughts, and trade winds also can affect the growing season. It is believed that the growing season for aquatic plants is roughly the same as for plants grown on the land.

It is believed that most green water plants, including most algae, use either red-orange light (around 6500 Angstroms) or blue-violet light (around 4500 Angstroms) in the photosynthesis process. Therefore, the dye used preferably should absorb a substantial portion of the light it receives at or near those wavelengths. The ideal dye undoubtedly would be a green dye of the same shade as the plants whose growth is to be controlled. However, green is not a particularly pleasing color for the water. Blue dyes are believed to have acceptable light screening characteristics, and they have the advantage that they give a pleasing coloration to the water. For this reason, it is preferred to use either a blue dye alone, or a combination consisting of a major portion of blue dye with a minor portion of a yellow dye. The yellow dye improves absorption in the blue region of the spectrum, and merely applies a slight greenish tint to the pleasing blue color given by the blue dye.

It is preferred that the light-fast quality of the dye should be relatively good in order to make it longer lasting when dissolved in the water. Of course, the dye should be water-soluble.

The dye or dye combination must be chemically non-toxic to animal life, including humans, fish and livestock. Also, the dye preferably is chemically non-toxic to plant life; it is preferred that the growth-controlling characteristics of the dye be due strictly to the light-screening action of the dye.

The following are preferred examples of suitable water-soluble blue, green or yellow dyes:

1. Colour Index Acid Blue 34; Ref. No. 42645

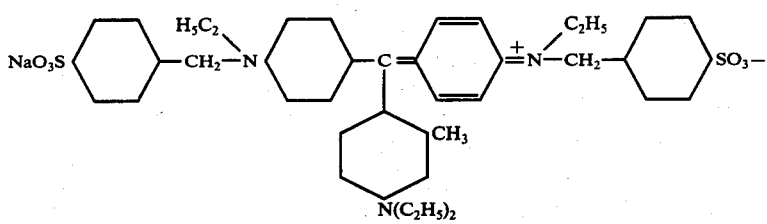

2. Colour Index Acid Blue 9; Ref. No. 42090 Other Names: C.I. Food Blue 2; Food, Drug and Cosmetic Blue 1 (FD&C Blue 1)

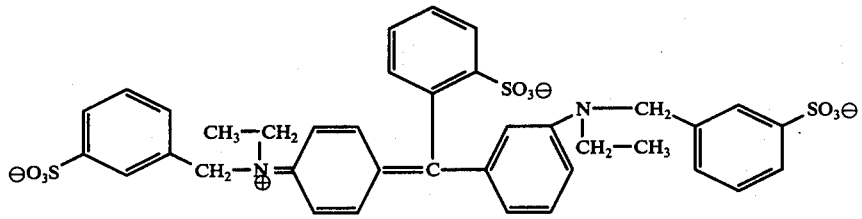

3. Colour Index Acid Blue 5; Ref. No. 42052 Other Names: D&C Blue 7 (Sodium Salt); D&C Blue 8 (Calcium Salt)

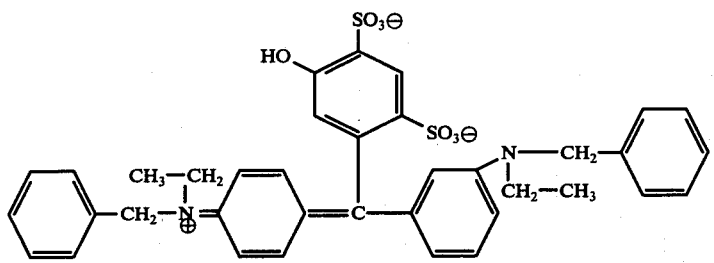

4. Colour Index Food Yellow 3; Ref. No. 15985 Other Names: FD&C Yellow 6

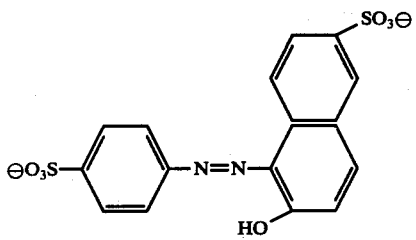

5. Colour Index Acid Yellow 23; Ref. No. 19140 Other Names: C.I. Yellow 4, FD&C Yellow 5, Tartrazine.

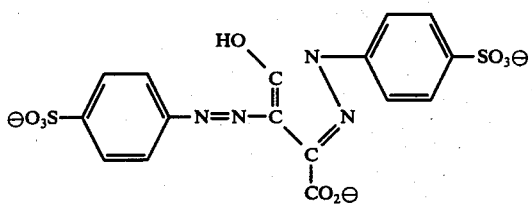

It is preferred that one of the foregoing blue dyes be mixed with one of the foregoing yellow dyes in a proportion such that the dye has an attractive blue-green coloration and gives that coloration to the water in which it is placed.

Other suitable dyes are listed in the following tables:

TABLE I

SUITABLE DYES

| Colour Index No. | *Light-Fast Normal | Colour Index Name | Comments |
|---|---|---|---|
| 42650 | 1 | Food Violet 1 | Bright Bluish Violet |
| 42650 | 1 | Acid Violet 17 | Bright Bluish Violet |
| 16580 | 4 | Acid Violet 3 | Bluish Violet |
| 15715 | 4–5 | Acid Black 34 | Bluish Grey |
| 17560 | | Acid Black 84 | Grey |
| 26310 | 5 | Acid Black 27 | Brownish Black |
| 27065 | Unknown | Acid Black 20 | Violet Black |
| 20350 | 5–6 | Acid Black 17 | Reddish Black |
| 26990 | 7 | Acid Black 32 | Greenish Black |
| 27510 | 6–7 | Acid Black 5 | Black |
| 20470 | 7 | Acid Black 1 | Bluish Black |
| 65008 | Unknown | Acid Black 97 | Greenish Grey |
| 27275 | 6 | Acid Black 36 | Greenish Black |
| 42055 | 2 | Acid Green 7 | Bright Bluish Green |
| 42055 | 2 | Solvent Green 15 | Bright Green |
| 42085 | 2 | Acid Green 3 | Bright Green |
| 42085 | 2 | Food Green 1 | Bright Green |
| 11838 | 6–7 | Acid Green 62 | Brownish Olive |
| 10020 | 6–7 | Acid Green | Yellowish Green |
| 42045 | 1 | Acid Blue 1 | Bright Greenish Blue |
| 42045 | 1 | Food Blue 3 | Bright Blue |
| 42645 | 1 | Acid Blue 15 | Bright Blue |
| 50230 | 3 | Acid Blue 18 | Reddish Navy |
| 16595 | 1 | Acid Blue 4 | Reddish Blue |
| 17185 | 4–5 | Acid Blue 6 | Navy |

*Scale is 1 to 8, with 8 being the best.

TABLE II

HUES

| Hue # | Light Fast | Hue # | Light Fast | Hue # | Light Fast |
|---|---|---|---|---|---|
| 3 | 1 | 5 | 3 | 7 | 1 |
| 8 | 6 | 9 | 1 | 11 | 2 |
| 23 | 5-6 | 26 | 1 | 27 | 4 |
| 32 | 2 | 38 | 2 | 40 | 5 |
| 52 | 4-5 | 58 | 4-5 | 70 | 4 |
| 74 | 1 | 81 | 5-6 | 103 | 3 |
| 106 | 6 | 25 | 3-4 | 128 | 4-5 |
| 148 | 2 | 150 | 4-5 | 158 | 5 |
| 158H | 5 | 171 | 6-7 | 175 | 6 |
| 185 | 5 | 197 | 8 | 275 | — |

Above are "Greenish Blue"

| Hue # | Light Fast | Hue # | Light Fast | Hue # | Light Fast |
|---|---|---|---|---|---|
| 10 | 2 | 13 | 1 | 16 | 2-3 |
| 17 | 1 | 19 | 3-4 | 28 | 1 |
| 31 | 2 | 56 | 5-6 | 57 | 6 |
| 59 | 3 | 62 | 5 | 65 | 4-5 |
| 84 | 2 | 88 | 2 | 89 | 4 |
| 92 | 4 | 101 | 4 | 124 | 5 |
| 126 | 4-5 | 131 | 6 | 149 | 1 |
| 156 | 5-6 | 166 | 6 | 170 | 6-7 |
| 206 | 3 | | | | |

Above are "Reddish Blue"

| Hue # | Light Fast | Hue # | Light Fast | Hue # | Light Fast |
|---|---|---|---|---|---|
| 8 | 6 | 20 | 4 | 29 | 7-8 |
| 30 | 2 | 60 | 2-3 | 87 | 3-4 |
| 94 | 5-6 | 114 | 5 | 115 | 2 |
| 118 | 5 | 172 | 3 | 173 | 3 |
| 177 | 6-7 | 184 | 6-7 | 187 | 6-7 |
| 194 | 6-7 | 201 | 7 | 202 | 7 |

Above are "Navy"

| Hue # | Light Fast | Hue # | Light Fast | Hue # | Light Fast |
|---|---|---|---|---|---|
| 9 | 2 | 11 | 3 | 12 | 6 |
| 13 | 2 | 19 | 3 | 20 | 3 |
| 25 | 5 | 27 | 6 | 30 | 3 |
| 31 | 4 | 33 | 3-4 | 34 | 2 |
| 35 | 5-6 | 37 | 5-6 | 39 | 1 |
| 40 | 5 | 44 | 6 | 48 | 3 |
| 50 | 2-3 | | | | |

Above are "Bluish Green"

| Hue # | Light Fast | Hue # | Light Fast | Hue # | Light Fast |
|---|---|---|---|---|---|
| 2 | 5 | 5 | 2-3 | 6 | 2 |
| 8 | 3 | 10 | 8 | 14 | 1 |
| 15 | 4 | 16 | 2 | 17 | 5 |
| 21 | 6 | 22 | 2 | 23 | 5-6 |
| 24 | 5-6 | 26 | 7 | 28 | 6 |
| 29 | 4 | 32 | 6-7 | 36 | 6 |
| 38 | 6 | 41 | 5-6 | 42 | 6 |
| 43 | 6-7 | 45 | 5-6 | 47 | 2 |
| 49 | 5 | 52 | 6 | 54 | 6 |
| 58 | 7 | 59 | 6-7 | 63 | 7 |
| 64 | 6 | 67 | 3 | 68 | — |

Above are "Green"

| Hue # | Light Fast | Hue # | Light Fast | Hue # | Light Fast |
|---|---|---|---|---|---|
| 4 | 6 | 46 | 5-6 | 55 | 4-5 |
| 57 | 6-7 | | | | |

Above are "Yellowish Green"

| Hue # | Light Fast | Hue # | Light Fast | Hue # | Light Fast |
|---|---|---|---|---|---|
| 65 | — | 103 | VG | 104 | 5 |
| 106 | — | 121 | — | 122 | — |
| 134 | 4-5 | 136 | 6-7 | 140 | 6-7 |

Above are "Grey"

| Hue # | Light Fast | Hue # | Light Fast | Hue # | Light Fast |
|---|---|---|---|---|---|
| 51 | 5 | 56 | mod. | 60 | 6-7 |
| 65 | — | 66 | 5 | | |

Above are "Brownish Olive"

| Hue # | Light Fast | Hue # | Light Fast | Hue # | Light Fast |
|---|---|---|---|---|---|
| 39 | 3 | 49 | 6-7 | 62 | 6-7 |
| 64 | 6-7 | 71 | — | | |

Above are "Greenish Grey"

| Hue # | Light Fast | Hue # | Light Fast | Hue # | Light Fast |
|---|---|---|---|---|---|
| 44 | 6-7 | 47 | 3 | 50 | 4 |
| 53 | 5-6 | 57 | 5-6 | 58 | 6-7 |
| 60 | 6-7 | 61 | 6-7 | 72 | — |
| 79 | 2 | 83 | 6 | 92 | 3-4 |
| 98 | 5-6 | 99 | 6 | 101 | 6 |
| 112 | — | 114 | 6 | 115 | 6 |
| 123 | — | 133 | 6 | 135 | 6 |
| 148 | 6-7 | 184 | — | | |

Above are "Bluish Grey"

| Hue # | Light Fast | Hue # | Light Fast | Hue # | Light Fast |
|---|---|---|---|---|---|
| 4 | 4 | 12 | 6 | 13 | 7-8 |
| 22 | 6 | 35 | 6 | 43 | 7-8 |
| 87 | 3-4 | 88 | 3 | 110 | — |
| 146 | 7 | 147 | 7-8 | | |

Above are "Reddish Black"

| Hue # | Light Fast | Hue # | Light Fast | Hue # | Light Fast |
|---|---|---|---|---|---|
| 14 | 7-8 | 15 | 6-7 | 49 | 6-7 |
| 54 | 6-7 | 70 | — | 73 | 3 |
| 85 | 3 | 95 | 3 | 96 | 3 |
| 108 | 7-8 | 144 | 3 | | |

Above are "Greenish Black"

| Hue # | Light Fast | Hue # | Light Fast | Hue # | Light Fast |
|---|---|---|---|---|---|
| 2 | 5 | 12 | 2 | 14 | 5 |
| 22 | 3 | 24 | 2 | 25 | 4-5 |
| 33 | 5 | 34 | 1-2 | 35 | 3-4 |
| 36 | 5 | 37 | 6 | 41 | 5 |
| 43 | 4 | 45 | 4 | 46 | 4-5 |
| 47 | 5 | 48 | 3 | 49 | 5 |
| 50 | 5 | 51 | 6-7 | 53 | 5-6 |
| 54 | 4-5 | 55 | 5-6 | 61 | 4 |
| 63 | 3-4 | 64 | 5-6 | 66 | 6 |
| 67 | 4-5 | 68 | 5-6 | 69 | 4-5 |

TABLE II-continued

HUES

| Hue # | Light Fast | Hue # | Light Fast | Hue # | Light Fast |
|---|---|---|---|---|---|
| 71 | 5-6 | 72 | 5-6 | 76 | 6 |
| 77 | 5-6 | 78 | 5 | 79 | 4 |
| 80 | 4-5 | 82 | 4 | 83 | 2-3 |
| 86 | 2 | 90 | 3 | 91 | 2 |
| 93 | — | 96 | 6-7 | 97 | 2 |
| 99 | 1-2 | 100 | 3 | 102 | 3-4 |
| 104 | 1 | 107 | 3 | 108 | 2 |
| 109 | 2-3 | 110 | 1 | 111 | 5-6 |
| 112 | 5 | 119 | 3 | 121 | 4 |
| 122 | 5 | 123 | 4-5 | 127 | 5 |
| 129 | 4-5 | 130 | 5-6 | 133 | 5-6 |
| 134 | 2 | 136 | 4-5 | 137 | 5-6 |
| 138 | 5 | 139 | 5 | 140 | 5-6 |
| 141 | 5 | 143 | 6 | 144 | 6 |
| 145 | 6 | 147 | 2 | 151 | 6-7 |
| 152 | 6-7 | 153 | 6 | 154 | 5 |
| 155 | 5-6 | 159 | 6 | 160 | 5-6 |
| 161 | 5-6 | 163 | 5 | 164 | 5-6 |
| 169 | 6-7 | 174 | 3 | 176 | 4-5 |
| 179 | 4-5 | 181 | 6 | 182 | 6 |
| 183 | 6 | 186 | 6-7 | 191 | — |
| 192 | — | 195 | 2 | 198 | 6 |
| 199 | 6 | 200 | 6-7 | 203 | 6 |
| 204 | 6-7 | 205 | 6 | 209 | 6 |
| 212 | 6 | 213 | 4 | 214 | 5-6 |
| 215 | 5-6 | 217 | 4-5 | 273 | — |
| 274 | — | 276 | — | | |

Above are "Blue"

| Hue # | Light Fast | Hue # | Light Fast | Hue # | Light Fast |
|---|---|---|---|---|---|
| 39 | 4 | 42 | 6-7 | 44 | 4-5 |
| 85 | 2 | 95 | 4-5 | 98 | 5 |
| 105 | 5 | 113 | 5 | 116 | 5 |
| 117 | 4 | 120 | 5 | 132 | 3 |
| 135 | 4-5 | 157 | 7 | 165 | 3-4 |
| 168 | 6-7 | 188 | 7 | 193 | 7 |
| 216 | — | | | | |

Above are "Reddish Navy"

| Hue # | Light Fast | Hue # | Light Fast | Hue # | Light Fast |
|---|---|---|---|---|---|
| 24 | 1 | 25 | 1 | 31 | 5 |
| 32 | 2 | 33 | 4-5 | 35 | 1-2 |
| 36 | 5 | 38 | 1 | 41 | 5 |
| 43 | 3 | 48 | 6 | 49 | 1-2 |
| 50 | 3 | 51 | 5 | 56 | 6 |
| 60 | 5 | 63 | 5-6 | 72 | 1 |
| 74 | 6-7 | 81 | 7 | 83 | 7 |
| 84 | 6-7 | 88 | 7 | 92 | 6-7 |
| 98 | 5-6 | | | | |

Above are "Bluish Violet"

| Hue # | Light Fast | Hue # | Light Fast | Hue # | Light Fast |
|---|---|---|---|---|---|
| 3 | 6 | 6 | 5 | 8 | 7 |
| 11 | 5 | 18 | 7-8 | 24 | 5 |
| 25 | — | 26 | 5 | 26A | 5 |
| 26B | 5 | 28 | 5 | 31 | 6 |
| 40 | 6 | 41 | 6-7 | 42 | 4 |
| 78 | 5 | 86 | 4 | 90 | 5-6 |
| 94 | 3 | 143 | 2-3 | | |

Above are "Bluish Black"

| Hue # | Light Fast | Hue # | Light Fast | Hue # | Light Fast |
|---|---|---|---|---|---|
| 2 | 4 | 7 | 3-4 | 9 | 5 |
| 10 | 6 | 16 | 8 | 19 | 6-7 |
| 21 | 6 | 23 | good | 29 | 3 |
| 30 | 6-7 | 33 | 6 | 37 | 4 |
| 38 | 4 | 51 | 5 | 52 | 7 |
| 55 | 6 | 56 | — | 59 | — |
| 63 | 7 | 67 | 4 | 68 | 3 |
| 77 | 3-4 | 89 | 3 | 102 | VG |
| 105 | — | 109 | — | 113 | 6 |
| 117 | 7 | 118 | — | 119 | — |
| 120 | — | 125 | 4 | 126 | 4 |
| 128 | 8 | 129 | 6-7 | 130 | 6-7 |
| 131 | 5-6 | 132 | 6 | 138 | 7-8 |
| 139 | 7 | 145 | 2-3 | 183 | — |
| 185 | — | | | | |

Above are "Black"

The hues in Table II can be matched to the dye in Table I by comparison of the color identification at the bottom of each hue group with the corresponding color in Table I. For example, the term "Greenish Blue" in the first section of Table II identifies those hues as Acid Blue 1 in Table I. Similarly, the hues in the "Navy" section are hues of Acid Blue 6.

In accordance with the present invention, the application rate of the dye is specified in terms of acre-yards; that is, in acres of surface area of water one yard deep. In this system of measurement, a body of water having one acre of surface area and having an average depth of 6 feet would have a volume of 2 acre-yards and would require the spreading of 2 pounds of dye over the surface of the lake in order to produce an application rate of one pound per acre-yard.

In the tests which have been performed, the growth of aquatic weeds has been reduced very significantly with an application rate of around one pound per acre-yard. However, the minimum application rate allowable in a particular body of water will have to be determined experimentally.

The dye is conveniently applied from the shoreline out to water depths of around six feet, unless it is known that weeds grow further out into the water. If algae grows throughout the lake, the treatment should cover the whole lake.

In lakes having substantial areas with depths greater than six feet, application of a dye in the manner described above, has the advantage that the concentration of dye in the weed-growing areas will remain sufficient over substantial time periods despite diffusion of the dye into untreated areas of the lake. One reason for this is that, by the foregoing method, a quantity of dye will be applied which will be sufficient to dye the whole lake. Thus, even though it is applied only in the shallower areas of the lake, diffusion into deeper waters cannot reduce the concentration of dye below the level necessary to stunt the growth of aquatic weeds. To cite an example, if a 10-acre lake of 18 feet average depth has a depth of 6 feet or under in only 30% of its area, 60 pounds of dye should be spread evenly over the 30% area, thus giving that area a much higher concentration than necessary, but permitting diffusion into the deeper waters without excessive reduction of light-screening powers.

The dye can be spread by merely scattering it over the water surface, or by placing it in a cheesecloth bag and suspending the bag in the water from a float, such as an inflated inner-tube for an automobile tire. The float is towed through the water, by means of a boat or from the shore, thus dissolving and spreading the dye.

An alternative method of application, in areas where sufficiently thick ice forms on the surface of the water, is one in which the dye powder is spread evenly over the surface of the ice just prior to the time of expected breakup of the ice. When the ice melts, the dye will slowly dissolve and diffuse into the water and will be present in the water in time to retard germination of the plants as the water warms up.

A better understanding of the present invention and of its many advantages will be had by referring to the following specific example, given by way of illustration.

EXAMPLE

A blue dye, believed to be Acid Blue 34, sold by the C. B. Dolge Company, Westport, Connecticut, under the name "Dolge Lake Dye" (for beautification purposes) was applied to a lake in Miami, Fla., in April, 1971. The lake was one acre in size and had an average depth of 5 feet. The dye was applied at the rate of approximately 2 pounds per acre over the entire surface of the lake. The dye gave the water a pleasing blue tint, and drastically reduced the growth rate of weeds in the lake. The same amount of dye was re-applied twice during the growing season, at four-month intervals. The lake remained virtually weed-free. The determination of this condition was made visually. There was no harm to land or aquatic animals.

The above description of the invention is intended to be illustrative and not limiting. Various changes or modifications in the embodiments described may occur to those skilled in the art and these can be made without departing from the spirit or scope of the invention.

I claim:

1. A method for controlling the growth of aquatic plants in a body of water, said method comprising coloring said water with a pigment of a predominantly blue color which absorbs predominantly light of a wavelength around 6500 Angstroms used by said plants for photosynthesis, at a time prior to maturity of said plants, by applying said pigment to said water in an amount sufficient to effectively arrest the growth of said plants, and repeating said coloring step, during the growing season for said plants, with a frequency directly related to the length of the growing season for said plants.

2. A method of controlling the growth of aquatic plants in a body of water, said method comprising spreading a dye in said water in the vicinity of growth of said plants, at a rate of at least one pound dry weight per acre-yard of water, thereby imparting a predominantly blue color to said water, prior to the maturity of said plants, said dye absorbing predominantly light of a wavelength around 6500 Angstroms, detecting the growth of said plants, and, at subsequent times during the growing season for said plants, repeating said dye spreading step when it is detected that said plants are growing at an undesirably fast rate.

3. A method as in claim 2 in which said dye is a blue dye.

4. A method as in claim 2 in which said dye absorbs a substantial portion of the light it receives at around 6,500 Angstroms, and at around 4,500 Angstroms.

5. A method as in claim 2 in which said blue dye is Acid Blue 9.

6. A method as in claim 2 in which a major portion of said dye is Acid Blue 9, and a minor portion of said dye is Acid Yellow 23.

7. A method as in claim 2 in which said spreading step consists of distributing the dye onto the surface of ice covering the water so that it will dissolve in the water when the ice melts.

* * * * *